US006214895B1

(12) United States Patent
Cercone

(10) Patent No.: US 6,214,895 B1
(45) Date of Patent: Apr. 10, 2001

(54) METHOD FOR MAKING A POLYVINYL ACETAL SPONGE PACKING FOR USE IN THE NASAL, SINUS AND OTIC CAVITIES

(75) Inventor: Ronald J. Cercone, East Lyme, CT (US)

(73) Assignee: Xomed Surgical Products, Inc., Jacksonville, FL (US)

( * ) Notice: Subject to any disclaimer, the term of this patent is extended or adjusted under 35 U.S.C. 154(b) by 0 days.

(21) Appl. No.: 09/661,896

(22) Filed: Sep. 14, 2000

Related U.S. Application Data

(62) Division of application No. 09/121,053, filed on Jul. 23, 1998, which is a division of application No. 08/778,141, filed on Jan. 2, 1997, now Pat. No. 5,843,060.

(51) Int. Cl.⁷ .............................. C08J 9/224; A61F 2/00; A61F 13/15
(52) U.S. Cl. ..................... 521/57; 424/423; 424/431; 424/445; 424/486; 521/78; 521/141; 523/122; 604/36; 604/37; 604/358; 604/363; 604/369
(58) Field of Search .................... 521/57, 78, 141; 424/486, 445, 431, 423; 523/122; 604/36, 37, 358, 363, 369

(56) References Cited

U.S. PATENT DOCUMENTS

| | | |
|---|---|---|
| 2,659,935 | 11/1953 | Hammon . |
| 2,664,366 | 12/1953 | Wilson . |
| 2,664,367 | 12/1953 | Wilson . |
| 3,390,671 | 7/1968 | Hildenbrand . |
| 3,695,989 | 10/1972 | Albert . |
| 3,783,872 | 1/1974 | King . |
| 3,892,905 | 7/1975 | Albert . |
| 4,066,488 | 1/1978 | von der Lehr . |
| 4,098,728 | 7/1978 | Rosenblatt . |
| 4,394,457 | 7/1983 | Ogasa . |
| 4,423,099 | 12/1983 | Mueller et al. . |
| 4,430,447 | 2/1984 | Pospich et al. . |
| 4,450,198 | 5/1984 | Michaels . |
| 4,466,431 | 8/1984 | Tharrat et al. . |
| 4,481,326 | 11/1984 | Sonenstein . |
| 4,544,693 | 10/1985 | Surgant . |
| 4,552,138 | 11/1985 | Hofeditz et al. . |
| 4,553,973 | 11/1985 | Edgren . |
| 4,642,267 | 2/1987 | Creasy et al. . |
| 4,656,216 | 4/1987 | Muller et al. . |
| 4,663,358 | 5/1987 | Hyon et al. . |
| 4,719,106 | 1/1988 | Shetty et al. . |
| 4,734,097 | 3/1988 | Tanabe et al. . |
| 4,847,324 | 7/1989 | Creasy . |
| 4,987,182 | 1/1991 | Creasy . |
| 5,001,009 | 3/1991 | Whitbourne . |
| 5,013,769 | 5/1991 | Murray et al. . |
| 5,071,648 | 12/1991 | Rosenblatt . |
| 5,139,510 | 8/1992 | Goldsmith, III et al. . |
| 5,147,899 | 9/1992 | Sato et al. . |
| 5,210,111 | 5/1993 | Goldenberg et al. . |
| 5,236,703 | 8/1993 | Usala . |
| 5,260,066 | 11/1993 | Wood et al. . |
| 5,262,475 | 11/1993 | Creasy . |
| 5,270,358 | 12/1993 | Asmus . |
| 5,284,468 | 2/1994 | Nelson . |
| 5,288,503 | 2/1994 | Wood et al. . |
| 5,370,656 | 12/1994 | Shevel . |
| 5,387,206 | 2/1995 | Valentine et al. . |
| 5,395,309 | 3/1995 | Tanaka et al. . |
| 5,422,050 | 6/1995 | Graiver et al. . |
| 5,447,505 | 9/1995 | Valentine et al. . |
| 5,466,231 | 11/1995 | Cercone et al. . |
| 5,556,391 | 9/1996 | Cercone et al. . |

FOREIGN PATENT DOCUMENTS 587902  12/1959  (CA) .

*Primary Examiner*—Morton Foelak

(57) ABSTRACT

Nasal, sinus and otic packings exhibiting a less adherent surface when in contact with tissue and being less traumatic on removal are prepared. In a first embodiment, polyvinyl acetal foamed packing material undergoes a surface modification imparting a non-adherent hydrogel coated surface. The surface modification is accomplished after final processing and fabrication of the packing product shape. The packing material is subjected to either an atomized spray of an aqueous solution of ethyl alcohol or a polyvinyl acetate/polyvinyl alcohol copolymer. In another embodiment, a foamed polyvinyl acetal material is produced by crosslinking polyvinyl alcohol with an organic compound containing two hydroxyl reactive groups in the presence of an inert gas. An aqueous solution containing polyvinylpyrrolidone is mixed into the reaction during crosslinking. The recovered sponge material foam product is cut or molded into a packing thereby resulting in the production of a packing having a uniformly dispersed gel throughout and as an outer hydrogel coating. Nasal, sinus and otic packings prepared by these methods exhibit a less adherent surface upon contact with tissue and are far less traumatic to the tissue upon removal.

6 Claims, 1 Drawing Sheet

METHOD FOR MAKING A POLYVINYL ACETAL SPONGE PACKING FOR USE IN THE NASAL, SINUS AND OTIC CAVITIES

CROSS-REFERENCE TO RELATED APPLICATIONS

This application is a divisional application of U.S. patent application Ser. No. 09/121,053, filed Jul. 23,1998, which is a divisional application of U.S. patent application Ser. No. 08/778,141, filed Jan. 2, 1997 and now U.S. Pat. No. 5,843,060, the disclosures of which are incorporated herein by reference.

BACKGROUND OF THE INVENTION

1. Field of the Invention

The present invention relates to a method for making non-sticking or nonadherent nasal, sinus and otic packings and other surgical packing shapes from treated polyvinyl acetal sponge material.

2. Discussion of the Related Art

The literature is replete with references to various types of foam materials including polyurethane, polyisocyanate, polystyrene, polyolefin, polyvinyl chloride, epoxy, urea-formaldehyde, latex, silicone, and fluoropolymer and with methods of controlling the physical properties of the foam or providing surface laminates on the foam surface during manufacture.

Advances in the development of synthetic polymers have produced radical changes in medical sponges. Factors such as water vapor, oxygen permeability, bacterial impermeability, and selective absorption can be incorporated into new formulations. These new formulations also address specific requirements such as conformability, non-adherence, and adhesiveness. Thus, a family of polymeric products has been formed for wound care including polymeric foams, polymeric films, particulate and fibrous polymers, hydrogels and hydrocolloids.

The optimum characteristic for nasal, sinus and otic packings is the ease of removal of the packing from the patient without pain or trauma. Wound dressings and other packing materials used for nasal, sinus and otic packings require a high degree of absorptivity. These packings normally swell as body fluids are absorbed. However, current materials and sponges such as porous foams support the coagulated blood and proteins exuding from the cavity surfaces that have been disrupted by surgery or trauma. These coagulated materials enter the pores of the sponge and dry in place. The coagulated blood and extudate form a mechanical bond with the sponge pores. When it is necessary to remove the sponge, the sponge can stick to the tissue surface via this connection. Removal of the medical sponge then causes debridement of the healing tissue surface causing pain and occasionally causing bleeding.

A number of solutions to the adhesion problem have been attempted. Overlays or coatings of silk, rubber or non-adherent films, such as polyethylene, have been applied to packings before insertion into the nasal cavity. Other techniques have included the application of lubricating gels, creams and ointments on the surface of the sponge packing material to alleviate patient discomfort upon packing withdrawal. None of these solutions have proven effective and adhesion of packing material continues to be a painful problem. There are a number of prior art references disclosing sponge dressings having varied treated surfaces.

A foam sponge product constructed of lyophilized hydrocolloid foam which is capable of absorbing body exudates is shown in U.S. Pat. No. 4,292,972. The wound dressing is preferably constructed with a thin outer oxygen and vapor-permeable film and a layer of an absorbent adhesive such as hydrogel for adhering the wound dressing to the skin and for acting as a reservoir for wound exudate absorbed therein. A layer of collagen, in the form of a sponge or film is adapted for placement directly on the wound, the collagen layer being of smaller dimensions than the absorbent adhesive layer so that areas of the adhesive layer extending beyond the periphery of the collagen layer can be applied to the skin surrounding the wound to adhere the dressing in place.

U.S. Pat. No. 3,934,587 discloses a solid sheet or film of a polymeric compound containing chemically reactable hydroxyl or amine groups that is reacted in a vapor phase mixture of acid chloride and aldehyde to form a product which is water-repellent on the treated side but water-permeable on the opposite, untreated side. The reactant sheet may be constructed of polyvinyl alcohol.

U.S. Pat. No. 4,997,425 discloses using a porous wound dressing including a first sponge layer for contacting a wound and a second surface remote from a wound. The second surface, the surface remote from the wound, has a pore size smaller than the first surface.

U.S. Pat. No. 4,054,141 describes a molded absorptive body including an absorptive layer of hydrophilic fibers and a sheath of the hydrophilic fibers bound together by thermoplastic particles. The absorptive body may be provided with a sheath on all sides or only on part of the body.

Sponges shaped for use as nasal, sinus and otic packings and other surgical packing shapes made from polyvinyl acetal sponge material are well known in the prior art. Polyvinyl acetal sponge packings can be treated and rendered hydrophilic. Such treated sponges have a great affinity for liquids and are soft and strong when moist. Such sponges present a gentle and non-traumatic packing material for use in body cavities or the like. Treated polyvinyl acetal sponge materials can be fabricated into shapes to provide hemostasis resulting from the tamponading effect of expansion from a compressed state. When used as nasal, sinus or otic packings, sponges are compressed and inserted into the nasal, sinus or ear cavity to arrest bleeding or restrain hemorrhage. The sponge is left in to absorb secretions and maintain the general pressure on the interior surfaces of the nasal, sinus or ear passages.

However, a problem that occurs with currently produced treated polyvinyl acetal packings inserted in the nasal, sinus or ear cavities is the mechanical debridement of the surgical site or cavity caused during healing by firm adhesion of the packing to the surgical site or to mucosal linings in the cavities via ingression of blood components serum, mucous and proteins. If the packing is left in situ for sufficient time, adhesions and actual connective tissue ingrowth and attachment will occur. This adhesion is caused by fibrin produced at the surgical site or in the nasal or sinus cavity and subsequent spreading of fibroblasts and capillaries. Although the polyvinyl acetal sponges may be rehydrated before removal, incrustation of the sponge surface with dried blood products and other exudate stiffens the sponge packings, adding to the difficulty of removal. Since the sponge expands to come into intimate contact with the wall of the nasal, sinus or ear passages having variable, asymmetrical spaces, such as are found in the nasal, sinus and ear cavities, the stiffened packings can assume a shape not readily withdrawn and removed without significant discomfort and pain for the patient.

Thus, there exists the need for a nasal packing, sinus packing and ear packing having a soft other surface and being advantageous for insertion into nasal, sinus and ear cavities. There is also another need for an easily removable nasal, sinus and otic packing to eliminate or reduce uncontrolled mechanical debridement of the nasal, sinus and otic cavity wall surfaces while still allowing removal of exudate from these surfaces and maintaining moisture at the packing interface.

Frictional and shear forces required by the physician to remove the device are lessened in the case of the soft, hydrogel surface or interface of the present invention.

OBJECTS AND SUMMARY OF THE INVENTION

Accordingly, it is a primary object of the present invention to provide a packing sponge for overcoming the adhesion or sticking problem encountered in removal of packing material from nasal, sinus and otic cavities.

It is a further object of the present invention to provide a non-stick, lubricious surface modification of polyvinyl acetal sponge material for use in nasal, sinus and otic packing sponges.

Another object of the present invention is to provide a method for producing a polyvinyl acetal sponge containing a uniformly dispersed interstitial gel of polyvinylpyrrolidone, for use in making nasal, sinus and otic packings, which overcomes the adhesion problem discussed above.

In a first embodiment, a polyvinyl acetal (PVAcl) packing material undergoes a surface modification, imparting a non-adherent hydrogel coating on the surface. The surface modification is accomplished after final processing and fabrication of the nasal packing product shape by subjecting the surface of the packing material to an atomized spray of an aqueous solution of ethyl alcohol. The bonds on the surface of the packing material formed by the reaction of hydroxyl groups with organic compounds containing aldehyde or dicarboxylic acid groups are degraded, thereby providing a surface layer of uncross-linked polymers by reverting to the base polymers, i.e., a hydrogel of a polyvinyl acetate/polyvinyl alcohol copolymer blend.

In the method of the second embodiment, a dried polyvinyl acetal sponge surface is treated with an atomizing spray of an aqueous solution containing a polyvinyl acetatelpolyvinyl alcohol copolymer blend to produce the desired hydrogel surface effect.

In the third embodiment of the present invention, a polyvinyl acetal sponge material is produced under high shearing mixing by cross-linking polyvinyl alcohol with one or more organic compounds containing carbonyl groups, such as aldehydes and/or dicarboxylic acids, in the presence of an inorganic acid catalyst. An addition of an aqueous solution of polyvinylpyrrolidone (PVP) is made into the reaction mixture during the production of polyvinyl acetal and the reaction is allowed to proceed until such time as 25% to 55% of the available active hydroxyl sites of the polyvinyl alcohol are bound. This process produces a lubricious surface on the packing sponge material and a uniformly dispersed gel in the interior of the packing sponge material. The final configuration of the product may be determined by either the shape of the container or mold, or the PVP impregnated packing material may be sliced into sheets and cut into final shapes.

Nasal, sinus and otic packings prepared by these methods exhibit a less adherent surface in contact with nasal, sinus and ear cavity walls. The removal of these packings having improved non-sticking characteristics is far less traumatic to the cavity linings than conventional packings.

The foregoing and additional objects, features and advantages of the invention will become apparent to those with skill in the art from the following detailed description of a preferred embodiment.

DETAILED DESCRIPTION OF THE PREFERRED EMBODIMENTS

Figure 1:
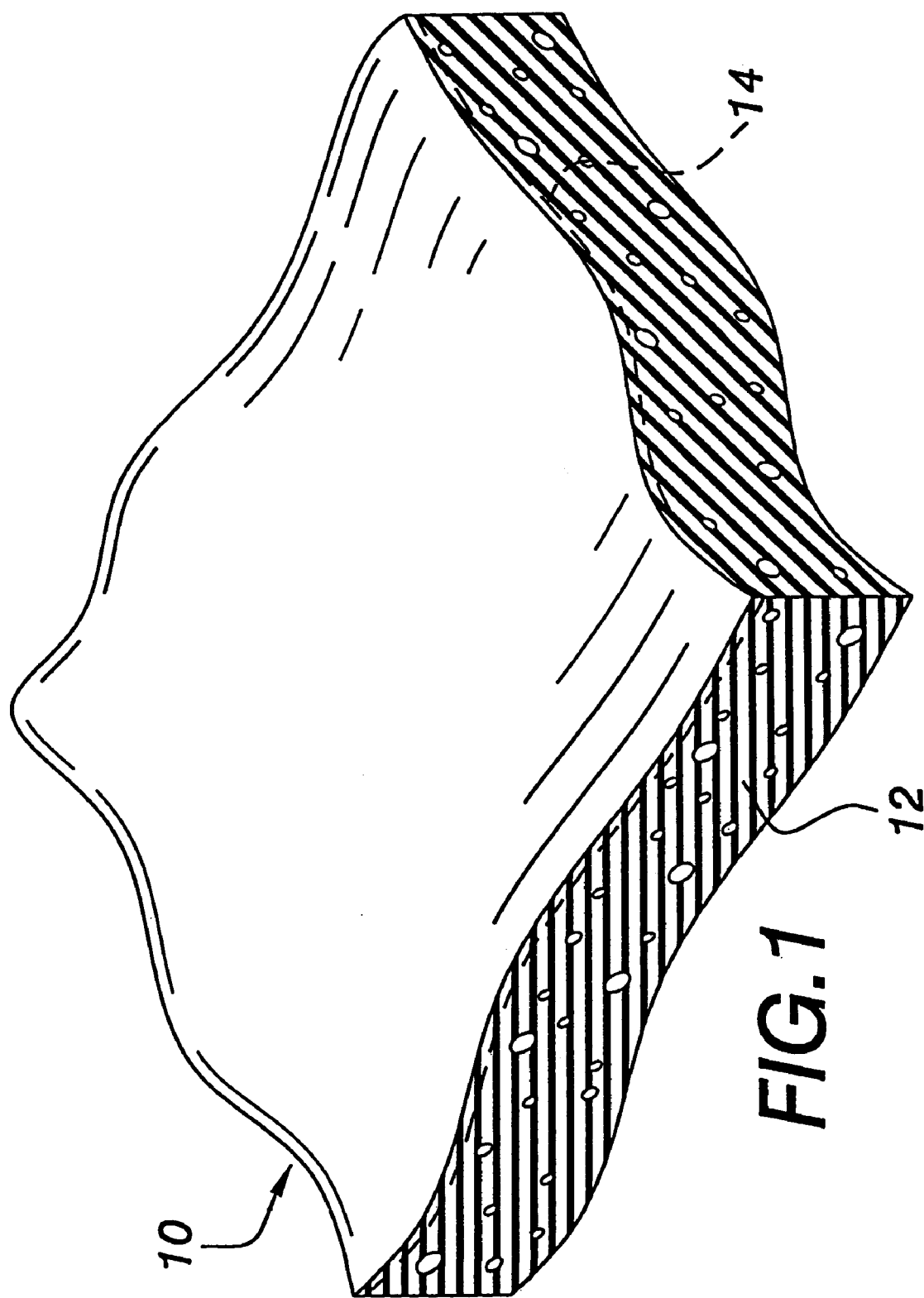
FIG. 1 shows a perspective view of a rectangular sponge packing having a lubricious, non-stick hydrogel surface layer.

In the method of the first embodiment, polyvinyl acetal (PVAcl) packing material undergoes a surface modification, thereby imparting a non-adherent hydrogel coating on the surface. The polyvinyl acetal sponge packing material preferably has a uniformly controlled pore size throughout its volume, is fast wicking, and has a high liquid holding capacity. Suitable polyvinyl acetal material is marketed under the trademark MEROCEL and is specifically described by U.S. Pat. No. 4,098,728, issued Jul. 4, 1978, which is incorporated herein by reference. The foam or sponge body of the invention is fabricated using commercially produced sponge products sold by Merocel Corporation under the grade designations CF50, CF100, CF150 and CF400. These grade designations have respective average pore diameters of 0.95 mm, 0.45 mm, 0.35 mm and 0.2 mm and an overall range of pore diameter of 0.004–1.2 mm. Certain of the grade designates have applications as medical sponges.

The preferred polyvinyl acetal material used in the present invention is a 15 mm thick Merocel CF50 polyvinyl acetal sponge material. This material is a homogeneous white, open-celled sponge with visible pores, instantaneous fluid wicking, absorptive capacity of up 25 times its weight in fluids, a retained fluid capacity of 16 times its own weight in fluids as measured by ASTM D-1117-80, and a pore size range (diameter) of 0.02 to 1.2 mm as determined by Scanning Electron Microscopy.

In the production of the polyvinyl acetal packings of the three present embodiments, polyvinyl alcohol is cross-linked in the presence of an inorganic acid catalyst with a linking agent selected from any suitable organic compounds containing two hydroxyl reactive groups, preferably carbonyl groups:

1) $C_1$-$C_{12}$ aldehydes and the like, such as formaldehyde and $C_2$-$C_{12}$ dialdehydes such as glutaraldehyde, most preferably formaldehyde;
2) $C_2$-$C_{12}$ dicarboxylic acids, such as succinic acid; and
3) a mixture of $C_1$-$C_{12}$ aldehydes and $C_2$-$C_{12}$ dicarboxylic acids For the purposes of description of the preparation of a polyvinyl acetal the following discussion is directed to the preferred mode of the invention through the use of formaldehyde as the linking agent. However, it is understood that any of the above recited organic compounds containing two hydroxyl reactive groups can be substituted for formaldehyde as the linking agent.

Polyvinyl alcohol and a linking agent, preferably formaldehyde, are reacted in an aqueous system having air bubbles uniformly dispersed therein in the presence of an inorganic acid catalyst. The reaction is preferably conducted in the presence of a non-toxic surfactant to aid in forming and stabilizing the gas bubbles formed uniformly throughout the reaction system. The reaction is carried out in two stages.

In the first stage, an aqueous dispersion of polyvinyl alcohol, an inorganic acid catalyst and a wetting agent are combined and are subjected to agitation, typically with beaters, at an elevated temperature to entrap air bubbles uniformly throughout the reaction system and to form a froth having a volume between 150 and 400% of the volume of the reactants in an unfrothed condition. Generally, it is preferred to add the surfactant and acid catalyst to an aqueous dispersion of the polyvinyl alcohol prior to the addition of the formaldehyde to produce packing sponge materials having a uniform pore size.

During the second stage, reaction between polyvinyl alcohol and formaldehyde is carried out while mixing is maintained during the well known bonding reaction of formaldehyde with pendant hydroxyl groups on polyvinyl alcohol chains to achieve a porous thin walled cell geometry and uniform pore distribution. After a froth is initially formed in the first stage, the formaldehyde, at elevated temperature, is added to the reaction system while continuing agitation in order to obtain a stable pore geometry necessary for high fluid capacity and fast wicking. The formaldehyde is added as an aqueous solution, generally about 37% aqueous to the reaction system while both the reaction system and the formaldehyde are maintained at an elevated temperature of between about 85° and 140° F., preferably between about 120° and 130° F. In this second stage, the agitation is continued until a stiff, pourable, or easily extrudable froth is formed as a result of the agitation. During agitation, the surrounding air is entrained in the reaction mixture to form the gas bubbles. Usually, entrainment of some relatively large bubbles accompanies the desired gas bubble size formation. In order to assure pore size uniformity and distribution, these large gas bubbles must be removed prior to curing the reaction. One method for removing these gas bubbles comprises reversing the direction of agitation and reverse mixing slowly so that they may rise to the surface and be removed from the reaction system. Alternatively, the froth can be extruded through a sieve or equivalent means such as a mesh screen to remove oversized gas bubbles from the froth. The froth is sufficiently stable as to substantially retain the size and distribution of gas bubbles.

After the froth is formed, the froth is cast into a warm mold for a sufficient period of time to cure the entire sponge composition. When the froth is placed into the mold, the mold is preferably at a temperature between about 120° to 130° F. so that the pore geometry size and distribution induced therein by the prior agitation step is substantially maintained. The mold and its contents are then preferably heated to a temperature of between about 100° and 120° F. and more preferably heated to between about 105° and about115° F., so that the exterior portion of the composition continues to cure relatively quickly and forms a framework to maintain the volume of the remainder of the foam during subsequent curing thereof. By following this procedure, it has been found that the uniformity of pore size distribution is maintained thereby. Thereafter, the remaining portion of the foam is cured at a temperature of between about 80° and about 130° F., preferably between about 80° and about 110° F., so that the remaining portion of the uncured foam cures uniformly. If the foam was cured at the higher initial curing temperatures only to accelerate the cure time, uneven curing would be observed since the foam is a relatively poor transmitter of heat from the exterior of the mold to the interior and the exterior of the foam would shrink excessively. Similarly, if curing is conducted at temperatures lower than these desired curing temperatures, the curing time would be excessive so that the gas bubbles would have time to merge into larger bubbles thereby destroying the uniformity and size of the desired pores.

The formaldehyde employed herein comprises aqueous solutions of formaldehyde. It has been found that certain other sources of formaldehyde, e.g. paraformaldehyde, contain toxic residues and are not desirable for forming the products of this invention unless converted to formaldehyde beforehand, since these toxic residues are more difficult to remove from the sponge product prior to use. In contrast, the formaldehyde remaining after reaction when employed as a pure aqueous solution is relatively easy to remove from the sponge by washing with water to obtain non-toxic levels of formaldehyde.

The preferred polyvinyl alcohols employed herein are medium molecular weight range polyvinyl alcohols in order to obtain uniformity of pore size. Generally, the medium molecular weight polyvinyl alcohols have an weight average molecular weight of between about 35,000 and about 45,000, more usually between about 39,000 and about 42,000. The molecular weight of polyvinyl alcohols can be determined by measuring the viscosity by means well known in the art.

Any inorganic acid catalyst may be employed in the process of this invention to catalyze the reaction of the formaldehyde and the polyvinyl alcohol. Organic acids such as toluene sulfonic acid are not useful in the process of this invention since they are more difficult to remove from the sponge product and, if present in the sponge product, would present a serious toxicological problem. Representative suitable inorganic acids include but are not limited to sulfuric acid, hydrochloric acid, phosphoric acid, nitric acid and the mixtures thereof. Generally, these acids are added as aqueous solutions to the reaction mixture and the amount of acid employed is generally between about 75 and about 200 weight percent based upon the weight of the polyvinyl alcohol.

The relative proportions of formaldehyde and polyvinyl alcohol are regulated so as to effect reaction of between about 25 and about 55%, preferably between about 30 and about 50% of the hydroxyl groups of the polyvinyl alcohol. When less than about 25% of the hydroxyl groups are reacted, the resultant sponge exhibits undesirably weak mechanical properties and, therefore, is not useful. In contrast, when more than about 55% of the hydroxyl groups are reacted, the resultant product is stronger but more abrasive to such a degree as to render it not reasonably useful as a medical packing.

The surfactants employed herein are those which promote formation of a stable froth in small quantities and do not present a serious toxicological hazard. Representative suitable surfactants include Tween 20, Tween 80, Triton X-100, Triton X-200 and sodium lauryl sulfates or the like. These surfactants are relatively non-toxic and can be removed subsequently from the sponge by washing. The surfactant is employed in amounts of between about 2 and about 6 weight % of polyvinyl alcohol. Increased amounts of surfactant result in stiffer polyvinyl acetal foams prior to curing and promote the formation of sponges having a relatively small pore size. In contrast, when employing relatively low amounts of the surfactant in the order of about 0.5 to about 2 weight % based upon the polyvinyl alcohol, the resultant sponge exhibits a relatively large non-uniform pore size. In any event, the surfactant is removed from the sponge after it is cured by washing with deionized water.

After the reaction mixture has been cured in the mold to form a polyvinyl acetal sponge, the sponge is removed therefrom and washed with deionized water and squeezed to remove the elutable unreacted formaldehyde, inorganic acid and surfactant. The alternate steps of washing and squeezing are repeated until substantially all of the elutable surfactant, formaldehyde and acid are removed from the sponge. High speed centrifugal extraction may be used as an alternative to squeezing. The alternate washing and drying steps are continued until a pH of 2–3 occurs in the washwater as measured by pH paper. Usually, this requires between about 10 to 15 sequential washings and squeezings. The preliminary washed sponge then is frozen and cut into smaller sponges of a desired shape in a manner so as to eliminate or minimize any lint formation, that might occur during the cutting operation. Cutting is preceded by freezing the damp sponge and then cutting the sponge with a cutting tool and in some cases cutting can be accomplished with high speed blades. It has been found that by freezing the liquid in the sponge, the friction on the cutting tool during cutting is minimized thereby minimizing lint formation resulting from fibers being torn from the sponge. The final washing steps are completed after freezing and cutting the sponge into desired shapes. The whole sponge or pieces from the cut sponge are dried in a manner so that upon rewetting and expansion they retain their general shape. It is essential that nasal and sinus packings maintain their general shape in both the wet and dry state since this characteristic is essential in some surgical procedures. For example, with nasal and sinus packings, it is necessary that the shape thereof be predictable in order to assure uniform absorption and contact with the liquid from the nasal and sinus cavities during surgery with no rough edges to catch on fine sutures.

Shape maintaining of the packing material while drying is effected by placing the sponge sheets between vapor-porous pads such as open celled polyurethane foam sheets and subjected first to a temperature of between 130° and 150° F. so that the outer surfaces of the sponge are quickly dried and rendered relatively stiff in comparison with the interior of the sponge. This procedure provides a relatively stable shape to the sponge being dried so that in a second step, the interior of the sponge can be subjected to moderate temperatures wherein the heat penetrates into the interior of the sponge uniformly to effect vaporization of the liquid therein out through the vapor-porous material. If such a procedure were not followed, the dried polyvinyl acetal sponge would not be subjected to heat uniformly and would distort during drying due to uneven shrinkage and, upon subsequent wetting of the sponge parts thereof, would expand non-uniformly.

A surface modification to the polyvinyl acetal (PVAcl) packing material is accomplished in the first two embodiments of the present invention after final processing and fabrication of the nasal, sinus or otic packing foam product shape. The shaped foam material is subjected to an atomized spray of a gelation inducing solution which, upon exposure to the surface of the polymeric packing material, splits or degrades the bond linkage created by the reaction of the linking agent, such as formaldehyde, with corresponding hydroxyl groups on polyvinyl alcohol chains at the surface polymer molecules of the packing material. As the bonds of the polyvinyl acetal are split, a gelatin occurs, thereby forming a molecular layer of uncross-linked polymers reverting to the base residue polymers, i.e., a hydrogel of a polyvinyl acetate/polyvinyl alcohol copolymer. Application rates of the aqueous gelation inducing solution range from about 5 to about 100 ml per ft$^2$ of polyvinyl acetal sponge packing surface.

In the method of the first embodiment, the formulation of the crosslink splitting spray solution is a solution of ethyl alcohol in water. The preferred concentration of ethyl alcohol in the solution is between about 20 percent and 60 percent by volume. The application rate of the solution must be controlled in order to prevent degradation of the polymeric acetal material beyond the surface layers of molecules in the sponge packing material. Preferred application rates of the ethyl alcohol solution range from about 10 to about 60 ml per ft$^2$ of packing surface. Application rates of other solution concentrations can be varied or adjusted accordingly as is known to those skilled in the art.

In a second embodiment, a coating is applied onto the sponge material without degrading the chemical structure of the surface of the polyvinyl acetal sponge. The total outer surface of the polyvinyl acetal sponge is treated with an aqueous spray solution or dispersion of a polyvinyl acetate/polyvinyl alcohol copolymer blend containing 0.1 to 0.5 parts by weight of polyvinyl acetate and 2 to 15 parts by weight of polyvinyl alcohol. This spray solution is prepared at a preferable concentration of between 1 percent and 20 percent by weight in water. This solution is prepared separately and applied by atomizing spray to the dried polyvinyl acetal sponge material in an over coating technique, thereby producing an equivalently functional surface effect, as compared to the surface coating produced using the first embodiment described above. Preferred application rates of the preferred polyvinyl acetate/polyvinyl alcohol copolymer blend aqueous solution range from about 5 to about 100 ml per ft$^2$ of polyvinyl acetal sponge packing surface. Application rates of other solution concentrations can be varied or adjusted accordingly as is known to those skilled in the art.

In the third embodiment of the present invention, a polyvinyl acetal material with a uniformly dispersed interstitial gel of polyvinylpyrrolidone is produced by a reaction for cross-linking polyvinyl alcohol in the presence of an inorganic acid catalyst with the above discussed linking agent selected from various organic compounds containing carbonyl groups, such as:

1) aldehydes including but not limited to: formaldehyde, as previously discussed in the sponge preparation, $C_2$–$C_{12}$ dialdehydes (i.e., glutaraldehyde and the like),
2) $C_2$ $C_1$ dicarboxylic acids (i.e., succinic acid and the like), or
3) a mixture of two or more of aldehydes and $C_2$–$C_{12}$ dicarboxylic acids.

The method for making the product of this third embodiment employs, in part, the well known, high-shear mixing methods for the production of polyvinyl acetals. The addition of a polyvinylpyrrolidone (PVP) aqueous solution, preferably having 1% to 10% by weight of PVP, during the process of polyvinyl acetal formation, as previously discussed, by the cross-linking reaction of PVA and an aldehyde or with a dicarboxylic acid or a mixture of an aldehyde and a dicarboxylic acid. The incorporation of polyvinylpyrrolidone (PVP) into the polyvinyl acetal (or dicarboxylic acid linked counterpart) produces an adequately lubricious surface on a sponge material formed from polyvinyl acetal (or dicarboxylic acid linked counterpart) having a uniformly dispersed PVP gel.

In an example formulation, the mixing sequence includes a number or steps. A first polyvinyl alcohol (PVA) solution is prepared by mixing polyvinyl alcohol, preferably at a concentration of from 1% to 30% by weight in water, with an inorganic acid catalyst. As previously discussed the inorganic acid catalyst and linking agent must be present in an amount suitable to effect reaction of between about 25 and about 55%, preferably between about 30 and about 50%, of the hydroxyl groups of the polyvinyl alcohol with the linking agent as would be readily apparent to one skilled in the art.

A second PVA solution is prepared by mixing PVA, at a preferred concentration of from 1% to 30% by weight, in water with an aldehyde and/or a dicarboxylic acid. These reactants and catalysts are incorporated in amounts and as compositions as previously discussed in polyvinyl acetal production.

The first and second solutions are mixed together rapidly at high shear while bubbling an inert gas through the mixing solutions. At a point during the mixing and crosslinking reaction, when about 10% to about 35% of the available hydroxyl groups of the polyvinyl alcohol are bound with the aldehyde and/or dicarboxylic acid, a third aqueous solution containing about 1% to 30% by weight of polyvinylpyrrolidone (PVP) is added to the reactive mixture containing the first two charged polyvinyl alcohol solutions containing either a linking agent or an inorganic acid catalyst. The volume of the third PVP containing solution is limited to a maximum of 25% of the total volume. The amount of PVP in the final recovered foam product should range between 0.1 and 0.8 percent by weight to the foam product. The reaction is then allowed to proceed until 25% up to about 55% of the available hydroxyl groups of the polyvinyl alcohol are reacted with the aldehyde or dicarboxylic acid. When utilizing a crosslinking reaction having a low degree of crosslinking, such as only crosslinking 25% of the available hydroxyl groups of the polyvinyl alcohol, one must would add the PVP charge into the crosslinking mixture at a crosslinking reaction point when only 10 to 15% of the available hydroxyl groups of the polyvinyl alcohol have been crosslinked. Accordingly, after the PVP charges are added, the reaction between the linking agents and the polyvinyl alcohol should preferably continue for an additional crosslinking reaction conversion of 10 to 40% of the available hydroxyl groups of the polyvinyl alcohol to ensure the interstitial impregnation of the PVP in the polyvinyl acetal.

The use of wetting aids, inorganic acid catalysts and other components may be incorporated into the PVP-PVAcl-PVA formulation as previously discussed in the preparation of polyvinyl acetal sponge materials.

As in the production of polyvinyl acetal sponge materials, the inclusion of the inert gas produces a frothed foam which is delivered to a container for final curing and cross-linking. After a curing period of a selected duration, three hours to 48 hours, at a selected curing temperature, 60° F. to 150° F., the cured material is washed with water to remove all reactants, thereby halting the progress of the reaction.

The final configuration of the product may be determined by either the shape of the container (or mold) or the material may be cut into sheets and final nasal packing shapes with dies or other cutting equipment, as is well known in the art. Any cutting of the PVP interstitially impregnated polyvinyl acetal will result in the exposure of a PVP coated surface.

While all of the above discussed foams are described as having a polyvinyl acetal structure, it must be recognized that the term polyvinyl acetal, and dicarboxylic acid derivatives thereof, as used herein also describes foams containing diester linkages formed from the reaction of dicarboxylic acid and hydroxyl groups of the polyvinyl alcohol.

Frictional and shear forces required by the physician to remove the packings are lessened in the case of a surface treated packing according to the methods of the present invention thereby resulting in reduced discomfort and pain experienced by the patient. The coefficient of friction is not only lower in the treated surfaces, but there is minimal opportunity for a three dimensional or geometric interlock relative to the direction of the packing device movement required for removal past dried blood clots or desiccated mucous. Nasal and sinus packings prepared by these methods exhibit a less adherent surface in contact with tissue. These packings are far less traumatic on removal and have improved non-sticking characteristics.

Fabrication of the inventive packing devices having a hydrogel surface treatment is preferably done by initial formation of the packing of the desired thickness by die cutting and mechanical compression followed by surface treatment with either the ethyl alcohol solution or the aqueous solution containing the copolymer blend of polyvinyl acetate and polyvinyl alcohol, followed by sterilization and packaging. Fabrication of the inventive PVAcl packing device containing PVP is preferably done by initial formation of sheets of the foam material of the desired thickness followed by die cutting, mechanical compression, fenestration, packaging and sterilization. This method insures a more uniform product, simplifies manufacturing operations and scale-up, and minimizes a lack of any lubricious, non-stick layer on any surface area on the packing body surfaces that are treated.

The processes of the present invention as shown in FIG. 1 produce a sterile compressed packing 10 constructed of an open cell foam material 12 having a pore diameter size which is not greater than 1.2 mm and having instantaneous wicking properties allowing the packing to swell and be free standing inside said cavity. The packing has an exterior lubricious, non-stick hydrogel surface layer 14 formed from: (a) a copolymer blend of polyvinyl acetate and polyvinyl alcohol or (b) polyvinylpyrrolidone. The hydrogel surface layer preferably has a thickness ranging from 0.0005 to 0.0030 inches for placement against a wall area in a body cavity. The hydrogel surface layer controls the absorbency of external fluids and debris into the open cell material and forms a substantially closed outer surface in relation to the open cell foam material, thereby reducing both the tissue attachment to the packing and the removal shear forces of the packing.

The foregoing describes the preferred embodiments of the present invention along with a number of possible alternatives. A person of ordinary skill in the art will readily recognize that modifications of the described embodiments may be made without departing from the true spirit and scope of the invention. The invention is, therefore, not restricted to the embodiments disclosed above, but is defined in the following claims.

What is claimed is:

1. A method for making a polyvinyl acetal sponge packing, for use in the nasal, sinus and otic cavities, with a lubricious, non-stick surface, said method comprising:

forming a polyvinyl acetal sponge material into a packing, wherein the packing has an exterior surface;

spraying a gelation inducing solution on said packing exterior surface, thereby creating upon said surface a layer of a hydrogel of a copolymer comprising a blend of polyvinyl acetate and polyvinyl alcohol.

2. The method of claim 1, wherein said gelation inducing solution comprises an aqueous solution of ethyl alcohol.

3. The method of claim 1, wherein said gelation inducing solution comprises an aqueous solution of 20% to about 60% by volume of ethyl alcohol.

4. The method of claim 1, wherein said gelation inducing solution comprises an aqueous solution of a copolymer blend of polyvinyl acetate and polyvinyl alcohol.

5. The method of claim 1, wherein said gelation inducing solution comprises an aqueous solution of about 1% to about 20% by weight a copolymer blend of polyvinyl acetate and polyvinyl alcohol.

6. The method of claim 1, wherein said gelation inducing solution is applied at an application rate in a range from about 10 to about 60 ml per $ft^2$ of packing surface.

* * * * *